United States Patent [19]

Katoh et al.

[11] Patent Number: 5,591,589
[45] Date of Patent: Jan. 7, 1997

[54] PROCESS FOR SEPARATING AND MEASURING GLYCOPROTEIN

[75] Inventors: Hideo Katoh; Kenji Nakamura; Shinji Satomura, all of Amagasaki, Japan

[73] Assignee: Wako Pure Chemical Industries, Ltd., Osaka, Japan

[21] Appl. No.: 340,299

[22] Filed: Nov. 14, 1994

[30] Foreign Application Priority Data

Nov. 16, 1993 [JP] Japan .................................. 5-309839

[51] Int. Cl.$^6$ ................................................. G01N 33/53
[52] U.S. Cl. ............................. 435/7.1; 435/7.9; 435/18; 435/973; 436/827; 530/412; 530/413
[58] Field of Search .............................. 435/7.9, 7.1, 18, 435/973; 436/827; 530/412, 413

[56] References Cited

U.S. PATENT DOCUMENTS

| | | | |
|---|---|---|---|
| 4,371,515 | 2/1983 | Chu | 436/544 |
| 4,389,392 | 6/1983 | Adachi | 424/1 |

FOREIGN PATENT DOCUMENTS

| | | |
|---|---|---|
| 0357869A1 | 3/1990 | European Pat. Off. . |
| 0441470A2 | 8/1991 | European Pat. Off. . |

OTHER PUBLICATIONS

Chemical Abst., vol. 118, No. 21, 1993 May 24, Columbus, OH; Katoh et al., "Analytical method for sugar chain structures involving lectins . . .", p. 470; 208 749p; J. Biochem (Tokyo) 1993, 113(1), 118–22.
Chemical Abst., vol. 115, No. 19, 1991 Nov. 11, Columbus, OH; Taniguchi et al., "Quantitative determination of sugar chains in glycoproteins . . .", p. 482; 202 251m; Seibutsu Butsuri Kagaku, 1991, 35(3), 199–204.
Chemical Abst., vol. 110, No. 19, 1991 May 8, Columbus, OH; Taketa et al., "Application of lectin affinity electro–phoresis . . .", p. 482; 202 251m; Rinsho Byori, Rinji Zokan 1988; (79), 140–8.
Aoyagi et al, Biochemica et Biophysica Acta, 830, (1985), pp. 217–223.

Primary Examiner—Toni R. Scheiner
Attorney, Agent, or Firm—Armstrong, Westerman, Hattori, McLeland & Naughton

[57] ABSTRACT

The degree of a structure change of the sugar chain of a glycoprotein caused by a disease can be measured with high precision rapidly by separating and measuring two or more forms of glycoproteins which are different in sugar chain structure but have substantially the same protein structure, by using a combination of a lectin capable of recognizing the specific sugar chain structure of at least one of these glycoprotein analytes to be measured, and a first antibody which has a property of binding to all the glycoprotein analytes but is kept from binding to glycoprotein analyte(s) having the lectin attached thereto; and separating and measuring glycoprotein analyte(s) having the first antibody attached thereto and glycoprotein analyte(s) having no first antibody attached thereto, by utilizing differences in properties between the former glycoprotein analyte(s) and the latter glycoprotein analyte(s).

7 Claims, 3 Drawing Sheets

PROCESS FOR SEPARATING AND MEASURING GLYCOPROTEIN

BACKGROUND OF THE INVENTION

This invention relates to a process for separating and measuring two or more forms of glycoproteins which are different in sugar chain structure.

In not only human beings but also most animals, many of proteins contained in body fluids are glycoproteins having one or more sugar chains. Recently, because of the diversity of its structure and the like, the sugar chain moiety is particularly noted as a substance carrying some information concerning the interior of a living body and is studied in many universities and research institutes both inside and outside Japan.

In the course of the study, a change in the sugar chain structure of a specific glycoprotein caused by some disease was often observed. For example, in human α-fetoprotein (AFP), it was confirmed that the addition of an α-L-fucose residue or an N-acetylglucosamine residue (bisecting N-acetylglucosamine) to AFP sugar chain is frequently observed with the progress of hepatic cellular carcinoma. Furthermore, the degree of such a change of the sugar chain structure is independent of the AFP concentration in serum and the change is confirmed even in early hepatic cellular carcinoma. Therefore, it is considered that the investigation of the degree of the change permits diagnosis of cancer. Thus, the change of the sugar chain structure is noted.

The degree of change of the sugar chain structure of a glycoprotein is measured mainly by an analytical method using a lectin, such as lectin column method or lectin electrophoresis method. The reason why the degree of change of the sugar chain structure is measured mainly by use of a lectin is, for example, as follows. Lectins are not expensive. Moreover, since the immunogenicity of the sugar chain moiety of a glycoprotein is lower than that of the protein portion of the glycoprotein, no effective anti-sugar chain antibody can be obtained except that for a part of the non-reducing terminal structure, namely, the preparation of an antibody to the sugar chain of the glycoprotein is very difficult.

However, although lectins have a high recognizing specificity for the sugar chain structure, their bonding strength (coupling constant) to the sugar chain is one over thousands to one over tens of thousands as high as that of the antibody. Therefore, it is difficult to form a complex of a lectin and the sugar chain which is stable like a complex formed by antigen-antibody reaction. Accordingly, when a lectin is used in place of an antibody in an analytical method requiring a washing procedure after the formation of a complex on a solid phase, such as an enzyme immunoassay (ELISA) using a solidified antibody, a complex of the lectin and a glycoprotein to be measured dissociates during the washing, resulting in causing problems such as a marked lowering of the measuring sensitivity. Thus, such a method cannot be said to be practical as a clinical diagnosis. In addition, because of the above-mentioned properties of lectins, there has been the following restriction: for measuring a glycoprotein by utilizing the reaction of a lectin with the glycoprotein, the measurement should be carried out in the presence of a large excess of the lectin over the glycoprotein to be measured, by use of a column coupled with the lectin, an agarose gel containing the lectin, or the like.

Therefore, there is desired the development of a process for rapid and easy separation and measurement of glycoprotein sugar chains, which has both the sugar-recognizing specificity of lectins and the high sensitivity of enzyme immunoassay.

SUMMARY OF THE INVENTION

This invention was made in view of such conditions and is intended to provide a process for high-sensitivity, rapid and easy separation and measurement of two or more forms of glycoproteins utilizing a lectin and an antibody.

This invention provides a separating and measuring process wherein analytes to be measured are two or more forms of glycoproteins which are different in sugar chain structure but have substantially the same protein structure, said process comprising reacting a sample containing two or more forms of glycoproteins with a lectin capable of recognizing the specific sugar chain structure of at least one of the glycoproteins to be measured, and an antibody which has a property of binding to all the analytes but is kept from binding to glycoprotein(s) having the lectin attached thereto (said antibody is hereinafter abbreviated as "first antibody"), and separating and measuring glycoprotein(s) having the first antibody attached thereto and glycoprotein(s) having no first antibody attached thereto, by utilizing differences in properties between the former glycoprotein(s) and the latter glycoprotein(s).

DESCRIPTION OF THE PREFERRED EMBODIMENTS

In the course of earnest study for developing a process for rapid and easy separation and measurement of two or more forms of glycoproteins, which have both the sugar-recognizing specificity of lectins and the high sensitivity of enzyme immunoassay, the present inventors found that antibodies which are kept from antigen-antibody reaction in the presence of a lectin (first antibodies) exist among antibodies to glycoproteins. As a result of further study for developing a separating and measuring process of two or more forms of glycoproteins utilizing such an antibody, the present inventors found that the degree of change in the sugar chain structure of a glycoprotein can be measured with high sensitivity by using a combination of a lectin capable of recognizing a structure change of the sugar chain of a glycoprotein caused by a disease, and an antibody having the above-mentioned property (a first antibody). Thus, this invention has been accomplished.

This invention is conducted, for example, as follows.

First, a sample derived from a living body and containing two or more forms of glycoproteins to be measured is reacted with a lectin capable of recognizing the sugar chain structure of at least one of these glycoprotein analytes to be measured, and a first antibody. Then, a complex of glycoprotein analyte(s) and the first antibody is separated from glycoprotein analyte(s) having no first antibody attached thereto, by utilizing differences in properties between the former and the latter, such as molecular weight difference, isoelectric point difference, electric charge difference, hydrophobicity difference, or the like. Thereafter, each of the former and the latter is measured by a method suitable for its properties.

Although the lectin and the first antibody may be reacted with the glycoprotein analytes to be measured, at the same time, it is preferable to react the lectin at first and then the first antibody because thereby the reaction of the lectin with glycoprotein analyte(s) is certainly caused, so that the precision of measurement is increased.

In the above-mentioned separation and measurement according to this invention, for facilitating the detection of the glycoprotein analytes to be measured, it is preferable to attach to the first antibody a substance capable of changing properties of the complex of glycoprotein analyte(s) and the antibody (said substance is hereinafter abbreviated as "separation-improving substance") or a labeling substance.

In addition, for facilitating detection of the glycoprotein analytes to be measured and measuring also the total amount of the glycoprotein analytes, it is preferable to co-use an antibody which can bind to all of the glycoprotein analytes including glycoprotein analyte(s) having the lectin attached thereto, and has a labeling substance attached thereto (this antibody is hereinafter abbreviated as "second antibody").

When the second antibody is used, this invention is conducted, for example, as follows.

First, a sample derived from a living body and containing two or more forms of glycoproteins to be measured is reacted with the second antibody, a lectin capable of recognizing the sugar chain structure of at least one of these glycoprotein analytes to be measured, and a first antibody. Then, a complex of glycoprotein analyte(s) and the first antibody is separated from glycoprotein analyte(s) having no first antibody attached thereto, by utilizing differences in properties between the former and the latter, such as molecular weight difference, isoelectric point difference, electric charge difference, hydrophobicity difference, or the like. Thereafter, each of the former and the latter is measured by utilizing properties of the labeling substance attached to the second antibody.

Although the second antibody, the lectin and the first antibody may be reacted with the glycoprotein analytes to be measured, at the same time, it is preferable to react the lectin (and the second antibody) at first and then the first antibody because thereby the reaction of the lectin with glycoprotein analyte(s) is certainly caused, so that the precision of measurement is increased.

The objective separation and measurement can be carried out with higher precision in some cases by treating the glycoprotein analytes to be measured, with glycosidase at the time of (or before) reacting the lectin and the first antibody or the second antibody with the glycoprotein analytes.

The reason is as follows. The outer chains of sugar chains of the glycoprotein analytes to be measured undergo various structural changes, depending on the kind of disease. Even when the sugar chains have a structure which essentially enables the lectin and the first antibody or the second antibody to bind to the sugar chains, the binding is hindered or impossible in some cases, depending on the kind of a sugar residue linked to the non-reducing terminal of the sugar chain. In this case, the precision of the objective separation and measurement can be increased by facilitating the binding of the lectin and the first antibody or the second antibody to glycoprotein analyte(s) having an objective structure, by treating the glycoprotein analytes to be measured, with a suitable glycosidase to remove the sugar residue at the non-reducing terminal properly at the time of (or before) reacting the lectin and the first antibody or the second antibody with the glycoprotein analytes to be measured.

The glycosidase used for this purpose is not particularly limited so long as it acts as sugar hydrolase. Preferable examples of the glycosidase are sialidase, β-galactodidase, β-N-acetylglucosaminidase, α-mannosidase, β-mannosidase, α-fucosidase, etc. The sources of these glycosidases are not particularly limited.

In the case described above, the conditions of the reaction with glycosidase, such as temperature and pH may be properly chosen depending on the kind of the glycosidase used. The reaction temperature is usually 0°–50° C., preferably 1°–40° C., more preferably 25°–37° C. The pH at the reaction is usually 2–10, preferably 4–9. The concentration of the glycosidase used is varied depending on the kind of the glycosidase used, and it is not critical so long as it is higher than a concentration at which the objective sugar hydrolysis reaction takes place. Carrying out the sugar hydrolysis reaction in a solution with a relatively high glycosidase concentration for a short time is preferable to carrying out the sugar hydrolysis reaction in a solution with a low glycosidase concentration for a long time because unnecessary removal of the sugar chains can be prevented. The concentration is chosen so as to adjust the total amount of the glycosidase in the reaction solution to usually 10 to 1,000 mU (unit), preferably 50 to 5,000 mU. The reaction time is usually 1 minute to 24 hours, preferably 3 minutes to 1 hour. When the reaction with the glycosidase is carried out simultaneously with the reaction with the lectin and the first antibody or the second antibody, the above reaction conditions are of course restricted by the reaction conditions for reacting the lectin and the like, to a certain extent.

The lectin used in this invention is not particularly limited, and one which has an ability to recognize an objective sugar chain structure may be properly selected from various lectins such as concanavalin A, *Lens culinaris* lectin, *Phaseolus vulgaris* lectin, *Datura stramonium* agglutinin, *Triticum vulgaris* lectin, etc.

As the first antibody (or an antibody used for preparing the second antibody) having the properties described above which is used in this invention, either of the following polyclonal antibodies and monoclonal antibodies may be used so long as they have the properties described above: e.g. polyclonal antibodies prepared by immunizing animals such as horse, cattle, sheep, rabbit, goat, rat, mouse, etc. with an analyte(s) to be measured, according to a conventional method, for example, the method described in Tadashi Matsuhashi et al. "Men-ekigaku Jikken Nyumon" 2nd ed., GAKKAI-SHUPPAN CENTER Ltd., 1981, etc.; and monoclonal antibodies produced by Hybridomas obtained by fusing cells from a tumor line of mouse together with mouse spleen cells previously immunized with an analyte(s) to be measured, according to the conventional method, i.e., the cell fusion method established by G. Kohler and C. Milstein (Nature, 256, 495, 1975). These polyclonal and/or monoclonal antibodies may be used singly or in proper combination of two or more thereof.

As the glycoprotein which can be separated and measured by applying this invention, any glycoprotein can be exemplified without particular restriction so long as it satisfies the following conditions: it is contained in a sample derived from a living body, for example, body fluids such as serum, blood, plasma or urine, lymphocyte, hemocyte, or any of various cells, it can have forms which are different in sugar chain structure but have substantially the same protein structure, and there exist a lectin capable of recognizing the specific sugar chain structure of at least one of the forms of glycoprotein to be measured and a first antibody. Preferable specific examples of the glycoprotein are enzymes such as amylase, alkaline phosphatase, acid phosphatase, γ-glutamyltransferase (γ-GTP), lipase, creatin kinase (CK), lactate dehydrogenase (LDH), glutamic-oxaloacetic acid transaminase (GOT), glutamic-pyruvic transaminase (GPT), renin, protein kinase, tyrosine kinase, etc.; physiologically active substances such as human chorionic gonadotropin (hCG), thyroid stimulating hormone (TSH), luteinizing hormone (LH), etc.; tumor associated antigens such as prostate gland specific antigen (PSA), α2-macroglobulin, carcinoembryonic antigen (CEA), α-fetoprotein, etc.; and glycogenic cancer antigens such as CA 19-9, CA 125, etc.

In the separating and measuring process of this invention, the concentration of the lectin used is varied depending on the kind of the lectin used, properties of the glycoprotein analytes to be measured, etc. It is preferable that the lectin is present together with the glycoprotein analytes in a concentration of usually 10 times or more, preferably 100 times or more, more preferably 1,000 times or more, as high as a set detection limit concentration of the glycoprotein analytes.

The concentration of the first antibody used is varied depending on a value at which the detection limit of the glycoprotein analytes to be measured is set. The concentration is preferably determined in view of the difference between the lectin and the first antibody in coupling constant for the glycoprotein analytes. Although the concentration is varied depending on, for example, the kinds and properties of the glycoprotein analytes and the lectin and properties of the first antibody, the concentration is preferably determined by utilizing, for example, the following general formula:

Concentration of the first antibody ≦ (coupling constant of the lectin)/(coupling constant of the first antibody)×(concentration of the lectin)

The coupling constant in the above general formula refers to a coupling constant obtained in the equilibrium reaction represented by the formula (1) described below and is calculated by the equation (2) described below:

$$[A]+[B] \leftrightarrow [A.B] \quad (1)$$

$$\text{Coupling constant} = [A.B]/([A] \times [B]) \quad (2)$$

wherein

[A]: the concentration (M) of the lectin or the first antibody in an equilibrium state,

[B]: the concentration (M) of free glycoprotein analyte(s) to be measured in an equilibrium state,

[A.B]: the concentration (M) of a complex of the lectin (or the first antibody) and glycoprotein analyte(s).

More specifically, for example, when the coupling constant of the lectin for the glycoprotein analytes is $1 \times 10^6$ $M^{-1}$ and the coupling constant of the first antibody for the glycoprotein analytes is $1 \times 10^8$ $M^{-1}$, the concentration of the first antibody is one-hundredth or less, preferably one-thousandth or less, as high as the lectin concentration.

Although the concentration of the first antibody used is preferably not less than a concentration at which the first antibody can bind to the whole of the glycoprotein analytes to be measured of a concentration corresponding to a set detection limit, it may be lower than (for example, about one-tenth) the above-mentioned concentration.

The concentration of the second antibody used is varied depending on a concentration at which the detection limit of the glycoprotein analytes is set. It is preferable to adjust the concentration of the second antibody in the reaction solution to a concentration which is not less than (preferably twice or more as high as, more preferably 5 times or more as high as) a concentration at which the second antibody can bind to the whole of the glycoprotein analytes of a concentration corresponding to the detection limit.

In the separating and measuring process of this invention, the reaction conditions for reacting the lectin, the first antibody and optionally the second antibody with the glycoprotein analytes to be measured, to form a complex of the lectin and glycoprotein analyte(s) and a complex of the first antibody and glycoprotein analyte(s) (or complexes of each of the above complexes and the second antibody) are not critical so long as they do not inhibit the formation of these complexes. The reaction may be carried out under reaction conditions employed for forming a complex or the like in a conventional method such as enzyme immunoassay (EIA), radioimmunoassay (RIA), fluoroimmunoassay (FIA) or affinity chromatography. For example, when a buffer solution is used in the reaction, as the buffer and other reagents, those used in the above conventional methods may be properly chosen. Although the pH at the reaction is not critical so long as it does not inhibit the formation of the above-mentioned complexes, it is usually 2–10, preferably 5–9. Although the temperature at the reaction is also not critical so long as it does not inhibit the formation of the complexes, it is usually 0°–50° C., preferably 0°–40° C., more preferably 0°–10° C. As to the reaction time, since the time required for the formation of the complexes varies depending on the reactivity of the glycoprotein analytes with the lectin, the first antibody and the second antibody, the reaction may be properly carried out for several seconds to several hours, depending on properties of these components.

As the separation-improving substance to be attached to the first antibody, any substance can be exemplified without particular limitation so long as it can change properties (e.g. molecular weight, hydrophobicity, isoelectric point, etc.) of the complex of glycoprotein analyte(s) and the first antibody. Preferable specific examples of the separation-improving substance are proteins such as α-chymotrypsinogen, β-galactosidase, lysozyme, cytochrome c, trypsin inhibitor, etc.; peptides containing amino acids such as phenylalanine, proline, arginine, lysine, aspartic acid, glutamic acid, etc.; halogen atoms such as bromine, chlorine, iodine, etc.; synthetic polymers such as poly(ethylene glycol)s, etc.; poly(amino acid)s such as poly(glutamic acid)s, poly(aspartic acid)s, poly(lysin)s, poly(arginine)s, poly(phenylalanine)s, poly(tyrosine)s, etc.; alkyl chains having 3 to 10 carbon atoms; fatty acids such as palmitic acid, oleic acid, stearic acid, etc.; and chemical substances which have a reactive group capable of binding to the first antibody and have hydrophobicity or ionicity, for example, N-(ε-maleimidocaproyloxy)succinimide (EMCS), N-succinimidyl-6-maleimidohexanoate, bismaleimidohexane (BMH), octylamine, etc. It is sufficient that the separation-improving substance used in this invention is properly chosen in view of properties (e.g. pH stability, hydrophobicity, solubility in an aqueous solution, isoelectric point, etc.) of the glycoprotein analytes to be measured and the first antibody.

As a method for combining the first antibody and the separation-improving substance which are used in this invention, there can be exemplified a method of linking the specific reactive group of the first antibody to the specific reactive group of the separation-improving substance; a method of replacing the specific reactive group of the first antibody by the separation-improving substance; and a method of combining the first antibody and the separation-improving substance through a substance having affinity for the first antibody (e.g. antibody, lectin, antigen, inhibitor, DNA, etc.). More specifically, there can be exemplified all of 1) conventional methods for attaching a labeling substance to an antibody which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawano "Zusetsu Keikokotai" 1st ed., Soft Science, Inc., 1983; and Eiji Ishikawa, Tadashi Kawai and Kiyoshi Miyai "Koso Men-eki Sokuteiho" 2nd. ed., IGAKU SHOIN Ltd. 1982), and 2) conventional methods for modification and attachment of substances (e.g. Ikuzo Uritani, Kensuke Shimura, Michinori Nakamura and Masaru Funazu "Tanpakushitsu-no Kagakushushoku <Jo> <Ge>" 1st ed., GAKKAI-SHUPPAN CENTER Ltd., 1981); Yuji Inada et al. "Poly(ethylene glycol) Syushoku Tanpakushitsu" Seikagaku Vol. 62, No. 11, pp. 1351–1362, Japanese Biochemical Association, 1990; and George H. K. and Mark M. M. "DNA PROBES" STOCKTON PRESS, 1989). The combination of the first antibody and the separation-improving substance may be carried out according to these method.

The labeling substance attached to the first antibody (or used for preparing the second antibody) according to this invention includes, for example, enzymes such as alkaline phosphatase, β-galactosidase, peroxidase, micro-peroxidase, glucose oxidase, glucose-6-phospate dehydrogenase, acetylcholinesterase, malate dehydrogenase, luciferase, etc., which are used, for example, in EIA; radioisotopes such as $^{99m}Tc$, $^{131}I$, $^{125}I$, $^{14}C$, $^3H$, etc., which are used, for example, in RIA; substances which can emit fluorescence, such as fluorescein, dansyl residue, fluorescamine, coumarin, naphthylamine, derivatives thereof, etc., which are used, for example, in FIA; luminescent substances such as luciferin, isoluminol, luminol, bis(2,4,6-trifluorophenyl) oxalate, etc.; substance which can absorb an ultraviolet light, such as phenol, naphthol, anthracene, derivative thereof, etc.; and substances having properties as spin labels, which are represented by compounds having an oxyl group, such as 4-amino-2,2,6,6-tetramethylpiperidin-1-oxyl, 3-amino-2,2,5,5-tetramethylpyrrolidin-1-oxyl, 2,6-di-t-butyl-α-(3,5-di-t-butyl-4-oxo-2,5-cyclohexadien-1-ylidene)-p-tolyloxy, etc. Needless to say, the labeling substance is not limited to these substances.

As a method for labeling the first antibody with the above-exemplified labeling substance, or a method for labeling an antibody with the above-exemplified labeling substance in order to prepare the second antibody, there can be exemplified all of conventional labeling methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawano "Zusetsu Keikokotai" 1st ed., Soft Science, Inc., 1983; and Eiji Ishikawa, Tadashi Kawai and Kiyoshi Miyai "Koso Men-eki Sokuteiho" 2nd. ed., IGAKU SHOIN Ltd. 1982). The labeling may be carried out according to these methods. Needless to say, a conventional method utilizing the reaction of avidin (streptoavidin) with biotin may be used as a labeling method.

When the glycoprotein to be measured in this invention is a substance which itself can be measured (detected) by some method, for example, an enzyme, it is of course possible to measure (detect) a complex of glycoprotein analyte(s) and the first antibody (and/or the second antibody) and glycoprotein analyte(s) having no first antibody attached thereto, by utilizing such a property of the glycoprotein itself. Needless to say, in this case, the measurement may be carried out according to a conventional enzyme activity determination method.

For separating and measuring a complex of glycoprotein analyte(s) and the first antibody (and/or the second antibody) and glycoprotein analyte(s) having no first antibody attached thereto, by utilizing differences between them in properties, a conventional column chromatographic technique or electrophoretic technique may be employed, though high-pressure liquid chromatography (HPLC) or capillary electrophoresis is preferably employed because they permit rapider and higher-precision separation and measurement.

When the complex is separated and measured by HPLC, the separation is carried out by HPLC using a column packed with a packing chosen depending on the difference in properties between the complex of glycoprotein analyte(s) and the first antibody (and/or the second antibody) and glycoprotein analyte(s) having no first antibody attached thereto, or on properties of the separation-improving substance in the case where this substance has been attached to the first antibody. Then, the separated complex and the like are measured by a measuring method suitable for their properties, or a measuring method suitable for properties of the labeling substance in the second antibody in the case where the second antibody is used. Thus, the amount of any of the glycoprotein analytes to be measured in a sample is determined.

As to the kind of the packing used in HPLC, it is sufficient that the packing is properly chosen depending on the difference in properties between the complex of glycoprotein analyte(s) and the first antibody (and/or the second antibody) and glycoprotein analyte(s) having no first antibody attached thereto, or properties of the separation-improving substance.

There is explained below in further detail a method for choosing the packing, depending on the difference in properties between the complex of glycoprotein analyte(s) and the first antibody (and/or the second antibody) and glycoprotein analyte(s) having no first antibody attached thereto, or properties of the separation-improving substance.

① When a Packing for Gel Filtration is Used

Since a packing for gel filtration has a property of separating an objective substance from other substances present together therewith by utilizing the difference between them in molecular weight, it can have a high separating capability when the molecular weight of the complex of glycoprotein analyte(s) and the first antibody (and/or the second antibody) is 1.2 times or more, preferably 1.5 times or more, more preferably 2 times or more, the molecular weight of glycoprotein analyte(s) having no first antibody attached thereto, or when the molecular weight ratio between the former and the latter can be adjusted to the above value by using a high-molecular weight substance such as a protein, synthetic polymer [e.g. poly(ethylene glycol)] or poly(amino acid) as a separation-improving substance. Therefore, in these cases, the packing for gel filtration is preferably used.

A separating method on the above principle which uses a separation-improving substance is particularly effective when a sample containing analytes to be measured contains various substances capable of affecting the analysis (e.g. serum) which are widely different in molecular weight.

In detail, to avoid the influences of substances present together with the analytes in the sample, it is sufficient that the molecular weight of the complex is higher than the maximum of the molecular weight of the substances capable of affecting the analysis. Therefore, it is sufficient that a separation-improving substance having a molecular weight satisfying this condition is chosen.

When the separating method using a separation-improving substance is employed, the complex containing analyte(s) to be measured is eluted in the void portion of a column when there is attached a separation-improving substance having a molecular weight higher than the cut-off molecular weight of a packing for gel filtration. Therefore, the analysis can be carried out in the short test time. In this case, needless to say, the separation-improving substance need not be a substance having a single molecular weight, namely, it is sufficient that the separation-improving substance is a substance having a molecular weight higher than the cut-off molecular weight of a packing for gel filtration.

The packing for gel filtration includes, for example, Wakosil 5Diol-200 (a trade name, Wako Pure Chemical Ind. Ltd.), Wakosil 5Diol-300 (a trade name, Wako Pure Chemical Ind. Ltd.), and TSK gel (a trade name, Tosoh Ltd.).

② When a Packing for Hydrophobic Chromatography is Used

Since a packing for hydrophobic chromatography has a property of separating an objective substance and other substances present together therewith by utilizing the difference between them in hydrophobicity, it can be used when the hydrophobicity of the complex of glycoprotein analyte(s) and the first antibody (and/or the second antibody) is different from that of glycoprotein analyte(s) having no first antibody attached thereto, or when there is used as separation-improving substance a substance which permits proper adjustment of the hydrophobicity of the complex, for example, a highly hydrophobic protein (e.g. α-chymotrypsinogen or β-galactosidase), a peptide containing a highly hydrophobic amino acid such as phenylalanine or proline, a homopolymer of a hydrophobic amino acid [e.g. poly(phenylalanine) or poly(tyrosine)], an alkyl chain having 3 to 10 carbon atoms, a halogen atom (e.g. bromine, chlorine or iodine), a highly hydrophobic chemical substance (e.g. octylamine, EMCS or BMH), a complex of a fatty acid such as palmitic acid, oleic acid or stearic acid.

When a peptide is used as a separation-improving substance, the peptide is preferably one which contains a highly hydrophobic amino acid, and it is sufficient that the hydrophobicity of the complex is adjusted by choosing the chain length of the peptide. When a peptide or a poly(amino acid), which is composed of a hydrophobic amino acid alone is used as a separation-improving substance, the number of residues of the amino acid is preferably 2 to 15 because the water-solubility of the peptide or the poly(amino acid) is lowered when the number of residues of the amino acid is more than 15. When a halogen atom is used as a separation-improving substance, the first antibody can easily be modified by direct halogenation, and the hydrophobicity of the complex can be adjusted by changing the amount of the halogen introduced. As the highly hydrophobic chemical substance, substances having a long alkyl chain can be exemplified in addition to the above-exemplified substances. When such a substance is used as a separation-improving substance, the hydrophobicity of the complex can be adjusted by choosing the length of the alkyl chain properly.

A separation-improving substance having too high a hydrophobicity is not desirable for the following reason. Since such a substance has a low water-solubility, an organic solvent should be used in the bonding reaction between the first antibody and the separation-improving substance, so that the following problem is caused in some cases: the resulting modified first antibody is denatured or decreased in activity, or it is water-insoluble.

The packing for hydrophobic chromatography includes, for example, Butyl-NPR (a trade name, Tosoh Ltd.), Butyl MCI gel (a trade name, Mitsubishi Kasei Corp.) and Phenyl MCI gel (a trade name, Mitsubishi Kasei Corp.).

③ When a Packing for Ion Exchange Chromatography is Used

In this case, an objective substance is separated from other substances present together therewith by utilizing the difference between them in ionicity. Therefore, a packing for ion exchange chromatography can be used when the ionicity of the complex of glycoprotein analyte(s) and the first antibody (and/or the second antibody) is different from that of glycoprotein analyte(s) having no first antibody attached thereto, or when there is used as separation-improving substance a basic protein (e.g. lysozyme or cytochrome c), an acidic protein (e.g. trypsin inhibitor), a peptide containing a residue of basic amino acid such as arginine or lysine or a residue of acidic amino acid such as aspartic acid or glutamic acid, a poly(amino acid) containing 50 or more of the above-exemplified amino acid residue, or a fatty acid (e.g. palmitic acid, oleic acid or stearic acid). In general, in ion exchange chromatography, a high separating capability and a high specificity can be attained when analytes to be measured are once adsorbed on a column and then eluted. Therefore, it is preferable to use a packing for cation exchange chromatography or a packing for anion exchange chromatography when a cationic separation-improving substance or an anionic separation-improving substance, respectively, is used.

When a peptide or a poly(amino acid), which is composed of only basic amino acid residues (or acidic amino acid residues) is used as a separation-improving substance, the elution time of the complex can be freely controlled by controlling the number of the amino acid residues. When there is used a peptide or a poly(amino acid), which is composed of usually 5 or more, preferably 50 or more, more preferably 100 or more, amino acid residues, the elution position of the complex can be completely separated from that of living body components in serum and urine. Therefore, the employment of such a peptide or poly(amino acid) is preferable. When the above-mentioned peptide or poly(amino acid) is a synthetic peptide or a synthetic poly(amino acid), the length and ionicity of the peptide, or poly(amino acid), is proportional to each other. Therefore, the elution positions of the complex and the like can easily be controlled by using as separation-improving substance a peptide, or a poly(amino acid), whose length has been properly controlled in its synthesis.

Even if a sample contains a plurality of serum components which affect the analysis, making the ionicity of the complex and the like larger than that of the serum components by use of a separation-improving substance is effective to avoid an affection to the analysis caused by serum components. In this case, the time required for the analysis can be reduced by utilizing a stepwise gradient, not linear gradient.

For separating the complex of glycoprotein analyte(s) and the first antibody (and/or the second antibody) from glycoprotein analyte(s) having no first antibody attached thereto, by ion exchange chromatography, it is preferable in some cases to treat the glycoprotein analytes to be measured with sialidase previously. In detail, when the sugar chain of the glycoprotein analyte has a sialic acid residue attached thereto at the end, in particular, when the sugar chain is a branched chain having 3 to 4 branches having a sialic acid residue attached thereto at the end, the separation of the complex of glycoprotein analyte(s) and the first antibody (and/or the second antibody) from glycoprotein analyte(s) having no first antibody attached thereto becomes insufficient in some cases owing to the influence of the carboxyl group of the sialic acid residue. Therefore, the previous treatment with sialidase is carried out for preventing this trouble.

Since a packing for ion exchange chromatography generally has a high exchange capacity (absolute adsorption capacity for ionic substance), the whole of the complex which has a separation-improving substance attached thereto, etc. can be adsorbed on the packing even in the analysis of a sample containing a large absolute amount of ionic substances together with analytes to be measured, such as a sample derived from a living body, for example, serum. Therefore, said complex can be eluted at a position at which the influence of the substances present together with the analytes can be substantially avoided. In addition, since the separation-improving substance usable in the present process has a high water-solubility, the water-solubility of the complex having the separation-improving substance attached thereto is higher than before the attachment. Therefore, in the present process, denaturation and deactivation of the analytes to be measured hardly occur during the formation of the complex having the separation-improving substance attached thereto.

The packing for ion exchange chromatography includes, for example, packings for anion exchange chromatography, such as DEAE-MCI gel (a trade name, Mitsubishi Kasei Corp.), QAE MCI gel (a trade name, Mitsubishi Kasei Corp.), Wako Beads DEAE gel (a trade name, Wako Pure Chemical Industries, Ltd.), POROS Q (mfd. by Perseptive Biosystems), POROS PI (mfd. by Perseptive Biosystems), etc.; and packings for cation exchange chromatography, such as SP MCI gel (a trade name, Mitsubishi Kasei Corp.), CM MCI gel (a trade name, Mitsubishi Kasei Corp.), Wako Beads CM gel (a trade name, Wako Pure Chemical Industries, Ltd.), POROS S (mfd. by Perseptive Biosystems), POROS CM (mfd. by Perseptive Biosystems), etc.

Although the complex of glycoprotein analyte(s) and the first antibody (and/or the second antibody) and glycoprotein analyte(s) having no first antibody attached thereto can be separated from each other and measured by HPLC using any of the above-mentioned chromatographies, the employment of ion exchange chromatography is most preferable in the present invention. The reason is, for example, as follows.

For example, for carrying out the separation and measurement by gel filtration chromatography, a column with a suitable length should be used. Therefore, the employment of gel filtration chromatography is disadvantageous in that it requires a longer separation time than does the employment of· ion exchange chromatography. Therefore, when the reduction of the separation time is required, ion exchange chromatography is preferably employed. Moreover, gel filtration chromatography is disadvantageous also in that it is not suitable for separating substances having a very high molecular weight (size of molecule: about 1,000 Å or more).

Hydrophobic chromatography, in some cases, causes the following problem: the activity of the glycoprotein analyte(s) in the complex is lost owing to the destruction of higher-order structure of the glycoprotein analyte(s) by an organic solvent used in the separation. For this reason, it is not desirable to use a highly hydrophobic substance as a separation-improving substance. Furthermore, there is a problem in that a complex of analyte(s) to be measured and a first antibody having a hydrophobic substance attached thereto as a separation-improving substance has a lowered water-solubility and hence is easily precipitated, so that its separation becomes difficult.

On the other hand, ion exchange chromatography permits more effective separation and measurement on the basis of the delicate difference in ionicity. Moreover, when ion exchange chromatography is employed, a separation-improving substance may be selected from substances various in ionicity, so that the separation and measurement of the glycoprotein analytes to be measured can be carried out at an optium pH. In addition, since the separation-improving substance used in ion exchange chromatography has a high water-solubility in itself, there is almost no fear that the attachment of the separation-improving substance to analytes to be measured may precipitate the analytes. Therefore, the separation can be stably carried out.

When the separating and measuring process of this invention is practiced using a separation-improving substance, an objective peak due to glycoprotein analyte(s) to be measured can be shifted to a position at which there is no influence of components of serum, urea, etc. Furthermore, the following effect can also be obtained: since the elution positions of complexes formed from various analytes to be measured can be made the same by choosing a separation-improving substance properly depending on the analytes, the various analytes can be measured using HPLC under the same analysis conditions.

In the present invention's separating and measuring process using a first antibody (and/or a second antibody) having a labeling substance attached thereto, the amount of the labeling substance contained in each of a complex of glycoprotein analyte(s) and the first antibody (and/or the second antibody) and glycoprotein analyte(s) having no first antibody attached thereto (including glycoprotein analytes having the second antibody attached thereto) which have been separated from each other by HPLC is determined by a predetermined method on the basis of the measurable (detectable) property of the labeling substance. When the glycoprotein analytes to be measured can be measured in themselves by some method, the amount of glycoprotein analyte(s) themselves contained in the complex and the amount of glycoprotein analyte(s) having no first antibody attached thereto (including glycoprotein analytes having the second antibody attached thereto) are determined by a predetermined method on the basis of the measurable (detectable) property of the glycoprotein analytes themselves. For example, when the property of the labeling substance or the glycoprotein analytes is enzyme activity, the determination is carried out according to a conventional method of EIA, for example, the method described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987, etc. When the labeling substance is a radioisotope, the determination is carried out according to a conventional method of RIA by properly choosing and using a measuring instrument such as GM counter, liquid scintillation counter, well-type counter, counter for HPLC, or the like, depending on the kind and intensity of a radiation emitted by said radioisotope (see, for example, Yuichi Yamamura, "Ikagaku Jikken Koza Vol. 8" 1st ed., NAKAYAMA-SHOTEN Ltd. 1971). When the property is fluorescence-emitting properties, the determination is carried out according to a conventional method of FIA using a measuring instrument such as fluorometer, for example, the method described in Akira Kawano "Zusetsu Keikokotai" 1st ed., Soft Science, Inc., 1983, etc. When the property is luminescence-emitting properties, the determination is carried out according to a conventional method using a measuring instrument such as photon counter, for example, the method described in Tsunehiro Kitagawa, Toshio Nanbara, Akio Tsuji and Eiji Ishikawa "Koso Meneki Sokuteiho", an extra issue No. 31 of Tanpakushitsu Kakusan Koso, pp. 252–263, KYORITSU-SHUPPAN Ltd., published on Sep. 10, 1987, etc. When the property is that of absorbing an ultraviolet light, the determination is carried out by a conventional method using a measuring instrument such as spectrophotometer. When the labeling substance is a substance having properties as spin labels, the determination is carried out according to a conventional method using an electron spin resonance apparatus, for example, the method described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 264–271, KYORITSU-SHUPPAN Ltd., published on Sep. 10, 1987, etc.

In the HPLC used for separating and measuring the complex of glycoprotein analyte(s) and the first antibody (and/or the second antibody) and glycoprotein analyte(s) having no first antibody attached thereto in the separating and measuring process of this invention, any apparatus can be used without any particular problem so long as it is usually used in the analysis field and has a constant flow rate.

A solvent (an eluent) used for separating and measuring the complex of glycoprotein analyte(s) and the first antibody (and/or the second antibody) and glycoprotein analyte(s) having no first antibody attached thereto, by HPLC is not critical so long as it neither decomposes the formed complex and the like into glycoprotein analyte(s) and lectin (or the first antibody) nor takes the property detectable by some method away from the glycoprotein itself or a labeling substance attached to the first antibody (and/or the second antibody). Usually, as the solvent, there is preferably used any of buffer solutions which are used in conventional methods such as EIA, RIA, FIA, affinity chromatography, etc. Preferable specific examples of the solvent are buffer solutions having a pH of 2 to 10 prepared by properly choosing, depending on properties of the complex and the like, the following materials, followed by addition and mixing: for example, buffers such as phosphates, acetates, citrates, Good's buffers, tris(hydroxymethyl)aminomethane, etc.; salts such as sodium chloride, potassium chloride, ammonium sulfate, etc.; polar organic solvents such as methanol, ethanol, isopropanol, acetonitrile, tetrahydrofuran, etc.; and surfactants.

In the separating and measuring process of this invention, for measuring the complex of glycoprotein analyte(s) and the first antibody (and/or the second antibody) and glycoprotein analyte(s) having no first antibody attached thereto, after their separation by HPLC, there is preferably employed the method comprising introducing an effluent from a column of HPLC into a detection section as it is, and directly measuring the amount of the glycoprotein itself or a labeling substance attached to the first antibody (and/or the second antibody), which is contained in the complex and the like in the effluent, which method is described, for example, in Shoji Hara and Akio Tsuji "Newest Liquid Chromatography" 1st ed., pp. 92–104, NANZANDO Ltd., published on Feb. 1, 1978. The reason is that this method permits rapid measurement. In this case, when the property detectable by some method of the glycoprotein itself or the labeling substance attached to the first antibody (and/or the second antibody), which is contained in the complex and the like is, for example, enzyme activity, a reaction section of so-called post-column method, in which a reagent for measuring the enzyme activity is added to the effluent to react therewith, should of course be provided between the column of HPLC and the detection section. As the reagent for measuring the enzyme activity which is used in the reaction section when the property is the enzyme activity, there may be used a reagent prepared by a conventional method, for example, a method based on the content of Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987, etc., or there may be properly chosen and used a reagent of a commercially available kit for clinical examination. Also when the property is other than enzyme activity, a suitable reaction section may be provided between the column of HPLC and the detection section in order to add and react a predetermined reagent for the purpose of increasing the detection sensitivity.

When a plurality of effluents different in components are used in the case of using HPLC in the separating and measuring process of this invention, elution may be carried out by either a concentration gradient method (a linear gradient method) or a stepwise method. But the stepwise method is preferable because it is advantageous, for example, in that it can be practiced by easy operations, can reduce the actual analysis time, and gives a sharp objective peak.

Needless to say, the separating and measuring process of this invention can be applied to immunoassay methods such as conventional EIA, RIA, FIA, etc.

This invention is more concretely explained below with reference to Examples, which are not by way of limitation but by way of illustration.

EXAMPLE 1

Separation and Measurement on the Basis of AFP Sugar Chain by Use of *Lens culinalis* Lectin (LCA)-A Lectin Solution As a lectin solution, there was used a solution prepared by dissolving LCA-A (available from Honen Corporation) in 50 mM 3-(N-morpholino)propanesulfonic acid (MOPS) buffer (pH 7.5) to a concentration of 1 mg/ml.

First Antibody Solution

Anti-AFP monoclonal antibody (available from Wako Pure Chemical Industries, Ltd.) which had been confirmed to have a property of binding to all AFP's but be kept from binding to AFP's having LCA-A attached thereto was treated into Fab' by a conventional method. A poly(aspartic acid) (average molecular weight: 28800, mfd. by Sigma Chemical Co.) was attached to the Fab' by a conventional method using N-(8-maleimidocapryloxy)sulfosuccinimide (mfd. by DOJINDO LABORATORIES) as a divalent crosslinking agent, to obtain anti-AFP-Fab' having the poly(aspartic acid) attached thereto (Fab'-pAsp). This Fab'-pAsp was added to 50 mM MOPS buffer (pH 7.5) to a concentration of 13.5 µM, whereby a first antibody solution was obtained.

Second Antibody Solution

Anti-AFP monoclonal antibody (available from Wako Pure Chemical Industries, Ltd.) which had been confirmed to have an antigen-recognition site different from that of the antibody used for preparing the first antibody solution, a property of binding to all AFP's, and an ability to bind also to AFP's having LCA-A attached thereto, was treated into Fab' by a conventional method. Horseradish peroxidase (POD, available from Toyobo Co., Ltd.) was attached to the Fab' by a conventional method using N-(8-maleimidocapryloxy)sulfosuccinimide (mfd. by DOJINDO LABORATORIES) as a divalent crosslinking agent, to obtain POD-labeled anti-AFP-Fab'. The POD-labeled anti-AFP-Fab' was added to 50 mM MOPS buffer (pH 7.5) to a concentration of 100 nM, whereby a second antibody solution was obtained.

Sample Solutions

Each of LCA-A attached type AFP (hepatic cellular carcinoma type AFP) and LCA-A non-attached type AFP (normal type AFP) was added to 50 mM MOPS buffer (pH 7.5, containing 0.2% W/V. bovine serum albumin) to a concentration of 100 ng/ml, whereby a hepatic cellular carcinoma type AFP solution and a normal type AFP solution, respectively, were prepared. Sample solutions were prepared by mixing the two AFP solutions in each of the ratios described in Table 1.

TABLE 1

| Normal type AFP solution | 100 | 90 | 85 | 80 | 60 | 40 | 20 | 0 |
|---|---|---|---|---|---|---|---|---|
| Hepatic cellular carcinoma type AFP solution | 0 | 10 | 15 | 20 | 40 | 60 | 80 | 100 |

* The figures in Table 1 indicate the mixing percentages (%) of the individual solutions.

HPLC Conditions

Figure 3:
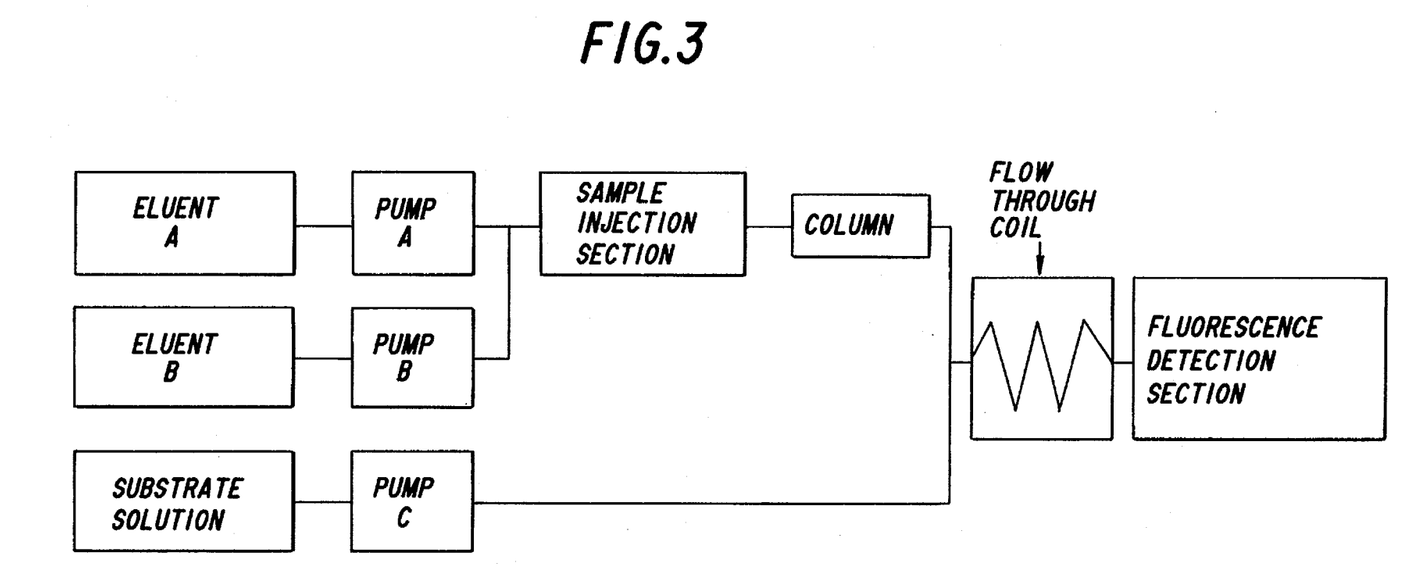
FIG. 3 is a schematic diagram showing the outline of a HPLC apparatus used in Example 1.

A diagram showing a HPLC system is given in FIG. 3.

Column: WAKOPAK MCI CQA-31S (4.6 mmID×10 mm).

Eluent A: 50 mM MOPS buffer (pH 7.5, containing 50 mM NaCl).

Eluent B: 50 mM MOPS buffer (pH 7.5, containing 1M NaCl).

Substrate solution: 50 mM MOPS buffer (pH 7.5, containing 100 mM 3-(p-hydroxyphenyl)propionic acid and 20 mM $H_2O_2$).

| Gradient: | 0–5 min. | eluent B 0% |
|---|---|---|
| | 5–8 min. | eluent B 20% |
| | 8–12 min. | eluent B 80% |
| Flow rate: | eluents A + B | 1 ml/min. |
| | substrate solution | 0.1 ml/min. |

Coloring coil temp.: 55° C.

Fuorescence detection: excitation wavelength 320 nm emission wavelength 404 nm

Measuring Procedure

To a mixed solution of 200 μl of the lectin solution and 10 μl of the second antibody solution was added 10 μl of each of the predetermined sample solutions, and the reaction was carried out at 10° C. for 15 minutes. To the reaction mixture was added 10 μl of the first antibody solution, and the reaction was carried out for another 2 minutes. Then, 100 μl of the thus obtained reaction mixture was analyzed by HPLC.

Results

Figure 1:
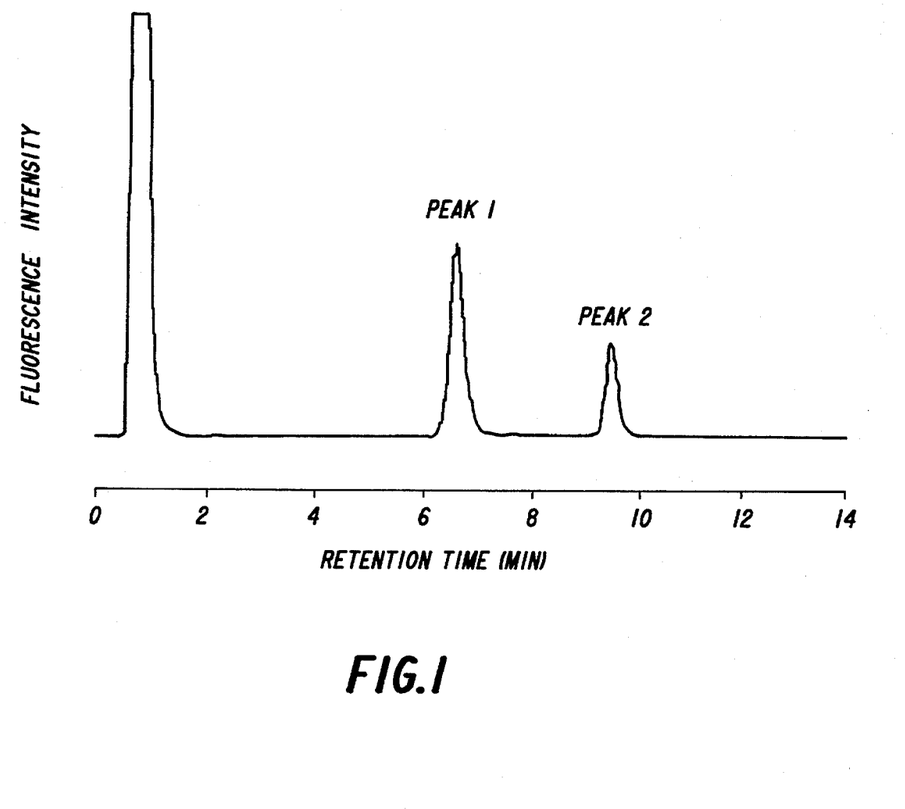
FIG. 1 shows a separation pattern obtained by high-pressure liquid chromatography (HPLC) in Example 1.

FIG. 1 shows a separation pattern obtained by the HPLC. In FIG. 1, peak 1 is due to AFP having no first antibody attached thereto, and peak 2 is due to AFP having the first antibody attached thereto.

Figure 2:
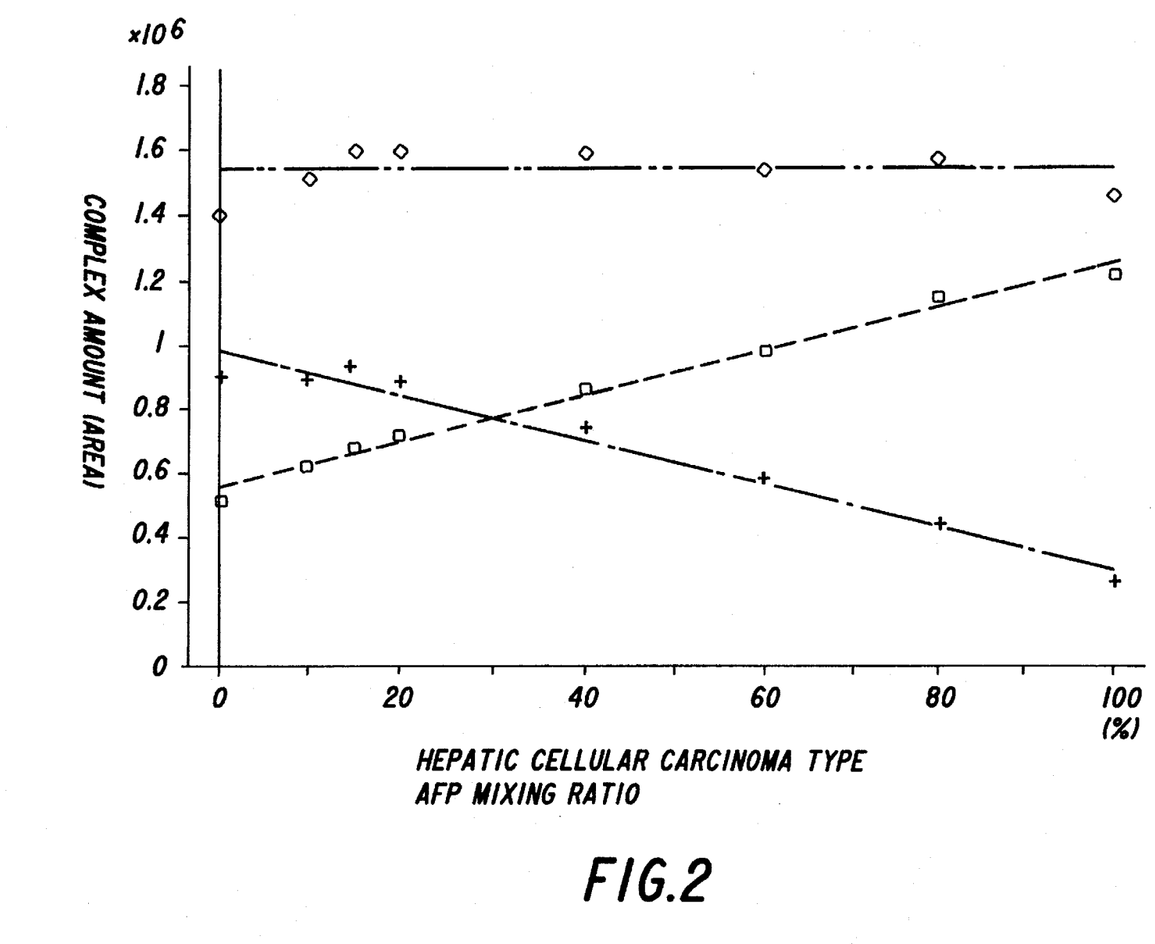
FIG. 2 is a graph obtained in Example 1 by plotting each of the area values of the two peaks in FIG. 1 obtained from each sample solution and the sum of the two peak areas, which correspond to the mixing ratio of a hepatic cellular carcinoma type α-fetoprotein (AFP) solution and a normal type AFP solution in each sample solution.

FIG. 2 shows peak area values of each of peaks 1 and 2 obtained from each sample solution and the sum of the two peak area values, which corresponded to the mixing ratio between the hepatic cellular carcinoma type AFP solution and the normal type AFP solution in each sample solution. In FIG. 2, □ shows the area value of peak 1, + the area value of peak 2, and ◊ the sum of the peak areas of peak 1 and peak 2.

The following is clear from the results shown in FIG. 2. The area value of peak 1 increases proportionately with an increase of the amount of the hepatic cellular carcinoma type AFP solution in the sample solutions, and the area value of peak 2 decreases proportionately with a decrease of the amount of the normal type AFP solution in the sample solutions, but the sum of the area values of peak 1 and peak 2 is substantially constant in the various sample solutions. In other words, by utilizing these two peak area values, the amounts of the hepatic cellular carcinoma type AFP contained in each sample solution and the total AFP concentration in the sample solution can be determined at the same time.

EXAMPLE 2

Change in Measured Value of the Fucose Addition Rate of AFP by Sialidase Treatment Sialidase Solution As a sialidase solution, there was used a solution prepared by dissolving sialidase (available from Toyobo Co., Ltd.) in 50 mM MOPS buffer (pH 7.5) to a concentration of 200 U/ml.

Lectin Solution

As a lectin solution, there was used a solution prepared by dissolving *Lens culinalis* lectin (LCA)-A (available from Honen Corporation) in 50 mM MOPS buffer (pH 7.5) to a concentration of 1 mg/ml.

Antibody Solution 1

Anti-AFP monoclonal antibody (available from Wako Pure Chemical Industries, Ltd.) competitive with LCA-A was treated into Fab' by a conventional method. A poly(aspartic acid) (average molecular weight: 28800, mfd. by Sigma Chemical Co.) was attached to the Fab' by a conventional method using N-(8-maleimidocapryloxy)sulfosuccinimide (mfd. by DOJINDO LABORATORIES) as a divalent crosslinking agent, to obtain anti-AFP-Fab' having the poly(aspartic acid) attached thereto (Fab'-pAsp). This Fab'-pAsp was added to 50 mM MOPS buffer (pH 7.5) to a concentration of 13.5 μM, whereby a first antibody solution was obtained.

Antibody Solution 2

Anti-AFP monoclonal antibody (available from Wako Pure Chemical Industries, Ltd.) noncompetitive with the antibody used for preparing antibody solution 1 was treated into Fab' by a conventional method. This Fab' was labeled with horseradish peroxidase (POD, available from Sigma Chemical Co.) by a conventional method using N-(8-maleimidocapryloxy)sulfosuccinimide (mfd. by DOJINDO LABORATORIES) as a divalent crosslinking agent, to obtain POD-labeled anti-AFP-Fab'. The POD-labeled anti-AFP-Fab' was added to 50 mM MOPS buffer (pH 7.5) to a concentration of 100 nM, whereby antibody solution 2 was obtained.

Sample Solutions

Three serum specimens of patients with hepatic cellular carcinoma in which the fucose addition rate had previously been measured by a lectin gel electrophoresis method using an AFP-lectin fractionating kit L (available from Wako Pure Chemical Industries, Ltd.) (operations were carried out according to the standard procedure described in a manual attached to the kit), were diluted with 50 mM MOPS buffer (pH 7.5, containing 0.2% bovine serum albumin) to adjust the AFP concentration to 100 ng/ml. The thus obtained dilutions were used as sample solutions 1, 2 and 3, respectively.

HPLC Conditions

A diagram showing the outline of a HPLC system is given in FIG. 3.

Column: WAKOPAK MCI CQA-31S (4.6 mmID×10 mm, mfd. by Wako Pure Chemical Industries, Ltd.)

Eluent A: 50 mM MOPS buffer (pH 7.5, containing 50 mM NaCl).

Eluent B: 50 mM MOPS buffer (pH 7.5, containing 1M NaCl).

Substrate solution: 50 mM MOPS buffer [pH 7.5, containing 100 mM 3-(p-hydroxyphenyl)propionic acid and 20 mM $H_2O_2$].

| Gradient: | 0–5 min. | eluent B 0% |
|---|---|---|
| | 5–8 min. | eluent B 20% |
| | 8–12 min. | eluent B 80% |
| Flow rate: | eluents A + B | 1 ml/min. |
| | substrate solution | 0.1 ml/min. |

Coloring coil temp.: 55° C.

Fuorescence detection: excitation wavelength 320 nm emission wavelength 404 nm

Measuring Procedure

After 10 μl of the sialidase solution, 100 μl of the lectin solution, 5 μl of antibody solution 2 and 10 μl of each of the predetermined sample solutions were mixed, the reaction was carried out at 10° C. for 3 minutes. To the reaction mixture was added 10 μl of antibody solution 1, and the reaction was carried out at 37° C. for another 4 minutes. After completion of the reaction, 100 μl of the reaction mixture was analyzed by HPLC under the above conditions.

That is, for each sample solution, the area of peak 1 (the peak of AP having no first antibody attached thereto) and the area of peak 2 (the peak of AFP having first antibody attached thereto) were obtained to give the peak 1 ratio (%) using the following equation:

$$\text{Peak 1 ratio (\%)} = \frac{\text{(Peak 1 area)}}{\text{(Total of peak 1 area and peak 2 area)}} \times 100$$

Further, the above-mentioned reaction was carried out using the solutions as mentioned above except for using 50 mM MOPS buffer solution (pH 7.5, containing 0.2% W/V of bovine serum albumin) containing 100 ng/ml of AFP with a fucose addition rate of 0% or AFP with a fucose addition rate of 100% in place of the sample solutions. The fucose addition rate was obtained using AFP-lectin fractionating kit-L (available from Wako Pure Chemical Industries, Ltd.). The resulting reaction solutions were analyzed by HPLC under the same procedures as mentioned above. For individual sample solutions, the peak 1 areas and the peak 2 areas were obtained to give the peak 1 ratios (%) using the above-mentioned formula. From the data obtained, a calibration curve showing a relationship between the peak 1 ratios and the fucose addition rates were obtained. By applying the peak 1 ratios obtained for the sample solutions 1, 2 and 3 to the calibration curve, the fucos addition rates of AFP in the sample solutions were obtained.

A reaction mixture obtained by carrying out the same reaction as above by use of the same solutions as above except for using 10 μl of 50 mM MOPS buffer (pH 7.5) in place of 10 μl of the sialidase solution, was also analyzed by HPLC under the above conditions. The fucose addition rates of AFP in the sample solutions were also obtained.

Results

As values of the fucose addition rate in the sample solutions 1 to 3, those obtained by the lectin gel electrophoresis method and those obtained by the above process of this invention are shown together in Table 2.

TABLE 2

| | Value obtained by | Fucose addition rate (%) measured by the process of the invention | |
|---|---|---|---|
| | lectin gel electrophoresis (%) | Sample untreated with sialidase | Sample treated with sialidase |
| Sample 1 | 20.8 | 65.9 | 28.9 |
| Sample 2 | 5.1 | 58.9 | 23.5 |
| Sample 3 | 6.1 | 51.2 | 3.7 |

As is clear from the results shown in Table 2, the removal of the sugar residue at the non-reducing terminal of AFP sugar chain by the sialiase treatment permits rapid and high-precision determination of the amount of AFP having fucose added thereto.

As is clear from the above, this invention provides a process which makes it possible to measure the degree of a structure change of the sugar chain of glycoprotein caused by a disease, with high precision rapidly and easily. The application of this invention is effective in that it becomes possible to give new information to diagnosis of cancer and the like which utilizes the degree of structure change of the sugar chain of glycoprotein. Therefore, this invention contributes greatly to the art.

What is claimed is:

1. A process for separating and measuring two or more forms of glycoproteins that are different in sugar chain structure but have substantially the same protein structure, which comprises reacting a sample containing two or more forms of glycoproteins with a lectin capable of recognizing the specific sugar chain structure of at least one of these glycoproteins to be measured, and a first antibody which has a property of binding to all the glycoproteins but does not bind to glycoprotein(s) having the lectin attached thereto; and separating and measuring glycoprotein(s) having the first antibody attached thereto and glycoprotein(s) having no first antibody attached thereto, by utilizing differences in properties between the former glycoprotein(s) and the latter glycoprotein(s).

2. A process according to claim 1, wherein the first antibody is labeled or has attached thereto, a substance capable of enhancing the separability of glycoprotein-first antibody complexes from glycoprotein lectin complexes.

3. A process according to claim 1, wherein a labeled second antibody which binds to all of the glycoproteins to be measured, whether or not the lectin is attached thereto, is used together with the lectin and the first antibody.

4. A process according to claim 1, wherein the glycoproteins to be measured are previously treated with glycosidase, or glycosidase is present when the glycoproteins are reacted with the lectin and the first antibody.

5. A process according to claim 3, wherein the glycoproteins to be measured are previously treated with glycosidase, or glycosidase is present when the glycoproteins are reacted with the lectin, the first antibody and the second antibody.

6. A process according to claim 1, wherein the differences in properties are differences in molecular weights, isoelectric points, hydrophobicity, or electric charges.

7. A process according to claim 1, wherein the concentration of the lectin is 10 or more times as high as a set detection limit concentration of glycoproteins and the concentration of the first antibody is equal to or lower than (the concentration of the lectin)×(coupling constant of the lectin)/(coupling constant of the first antibody).

* * * * *